United States Patent
Lim et al.

(10) Patent No.: US 10,610,189 B2
(45) Date of Patent: Apr. 7, 2020

(54) X-RAY IRRADIATING DEVICE INCLUDING MOTION SENSOR AND X-RAY IMAGING METHOD USING SAME

(71) Applicants: VATECH Co., Ltd., Gyeonggi-do (KR); VATECH EWOO Holdings Co., Ltd., Gyeonggi-do (KR)

(72) Inventors: Hyungkeun Lim, Gyeonggi-do (KR); Jinpyo Chun, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 141 days.

(21) Appl. No.: 15/567,962

(22) PCT Filed: Apr. 20, 2016

(86) PCT No.: PCT/KR2016/004101
§ 371 (c)(1),
(2) Date: Oct. 19, 2017

(87) PCT Pub. No.: WO2016/171462
PCT Pub. Date: Oct. 27, 2016

(65) Prior Publication Data
US 2018/0132813 A1    May 17, 2018

(30) Foreign Application Priority Data
Apr. 20, 2015    (KR) .......................... 10-2015-0055237

(51) Int. Cl.
*A61B 6/00* (2006.01)
*G06F 3/01* (2006.01)
(Continued)

(52) U.S. Cl.
CPC ................ *A61B 6/547* (2013.01); *A61B 6/08* (2013.01); *A61B 6/14* (2013.01); *A61B 6/145* (2013.01);
(Continued)

(58) Field of Classification Search
CPC .. A61B 6/547; A61B 6/08; A61B 6/14; A61B 6/145; A61B 6/4435; A61B 6/542; A61B 6/587; G06F 3/01
See application file for complete search history.

(56) References Cited

U.S. PATENT DOCUMENTS 5,572,567 A * 11/1996 Khutoryansky ..... A61B 6/4283
378/177
5,734,694 A    3/1998 Khutoryansky et al.
(Continued)

FOREIGN PATENT DOCUMENTS

JP    2010-075682 A    4/2010
JP    2012-130376 A    7/2012
(Continued)

OTHER PUBLICATIONS

English Translation of JP2014-226475A.*
(Continued)

*Primary Examiner* — David P Porta
*Assistant Examiner* — Djura Malevic
(74) *Attorney, Agent, or Firm* — IP Legal Services, LLC (57) ABSTRACT

Disclosed are an X-ray irradiating device having a function of selecting an automatic radiographic mode and an X-ray imaging method using the same. The X-ray irradiating device includes an X-ray source, a motion sensor configured to detect an X-ray source pointing direction, and a controller configured to select any one of a plurality of radiographic modes according to a pointing angle signal received from the motion sensor. The X-ray imaging method, which uses
(Continued)

| No. | Subject | | Radiographing Illustrates | Radiographic Angle Illustrates | Radiographic Angle |
|---|---|---|---|---|---|
| 1 | Anterior Teeth | | | | +45° |
| 2 | | Mandibular | | | -25° |
| 3 | Molar Teeth | Maxillary | | | +30° |
| 4 | | Mandibular | | | -5° |
| 5 | Occlusal Plane | | | | +5°~+8° | the above described X-ray imaging apparatus, includes setting a reference plane as a reference value for a pointing angle in which an X-ray source is directed, detecting the pointing angle relative to the reference plane by using a motion sensor and selecting a radiographic mode corresponding to the detected pointing angle, and performing a radiography by controlling the X-ray source with a set value corresponding to the selected radiographic mode.

15 Claims, 5 Drawing Sheets

(51) Int. Cl.
    *A61B 6/14*     (2006.01)
    *A61B 6/08*     (2006.01)

(52) U.S. Cl.
    CPC ............ *A61B 6/4435* (2013.01); *A61B 6/542* (2013.01); *A61B 6/587* (2013.01); *G06F 3/01* (2013.01); *A61B 6/4405* (2013.01); *A61B 6/4452* (2013.01); *A61B 6/463* (2013.01)

(56) References Cited

U.S. PATENT DOCUMENTS

| | | | | |
|---|---|---|---|---|
| 6,859,513 | B2* | 2/2005 | Sako | A61B 6/00 378/16 |
| 7,277,523 | B2* | 10/2007 | Mattson | A61B 6/032 378/15 |
| 7,324,622 | B2* | 1/2008 | Morikawa | A61B 6/032 378/15 |
| 7,545,907 | B2* | 6/2009 | Stewart | A61B 6/02 378/108 |
| 7,639,779 | B2* | 12/2009 | Kashiwagi | A61B 6/502 378/165 |
| 7,945,013 | B2* | 5/2011 | Goto | A61B 5/4869 378/16 |
| 7,978,813 | B2* | 7/2011 | Yoshimura | A61B 6/14 378/38 |
| 7,983,457 | B2* | 7/2011 | Toth | A61B 6/032 378/16 |
| 8,005,284 | B2* | 8/2011 | Sakaguchi | A61B 6/4441 382/131 |
| 8,064,569 | B2* | 11/2011 | Arai | A61B 6/032 378/108 |
| 8,300,765 | B2* | 10/2012 | Gotman | A61B 6/032 378/62 |
| 8,744,039 | B2* | 6/2014 | Hirokawa | A61B 6/032 378/108 |
| 9,107,591 | B2* | 8/2015 | Gotman | A61B 6/032 |
| 2006/0140333 | A1* | 6/2006 | Sommer | A61B 6/032 378/4 |
| 2006/0215817 | A1* | 9/2006 | Watanabe | A61B 6/4441 378/114 |
| 2007/0189438 | A1* | 8/2007 | Popescu | A61B 6/025 378/4 |
| 2007/0269011 | A1* | 11/2007 | Sandkamp | A61B 6/4441 378/114 |
| 2007/0287901 | A1* | 12/2007 | Strommer | A61B 5/0066 600/407 |
| 2009/0103685 | A1* | 4/2009 | Abe | A61B 6/06 378/147 |
| 2009/0175413 | A1* | 7/2009 | Sung | A61B 6/06 378/64 |
| 2010/0067650 | A1* | 3/2010 | Arai | A61B 6/032 378/16 |
| 2010/0329430 | A1* | 12/2010 | Zeng | A61B 6/00 378/165 |
| 2012/0155605 | A1* | 6/2012 | Yazaki | A61B 6/488 378/8 |
| 2013/0294569 | A1* | 11/2013 | Yoshikawa | A61B 6/032 378/4 |
| 2014/0010349 | A1* | 1/2014 | De Godzinsky | A61B 6/06 378/62 |

FOREIGN PATENT DOCUMENTS

| | | |
|---|---|---|
| JP | 2013-248384 A | 12/2013 |
| JP | 2014-226475 A | 12/2014 |
| KR | 10-0850500 B1 | 8/2008 |

OTHER PUBLICATIONS

European Patent Office, Extended European Search Report of corresponding EP Patent Application No. 16783395.3, dated Jan. 3, 2019.

* cited by examiner

| No. | Subject | | Radiographing Illustrates | Radiographic Angle Illustrates | Radiographic Angle |
|---|---|---|---|---|---|
| 1 | Anterior Teeth | Maxillary | | | +45° |
| 2 | | Mandibular | | | -25° |
| 3 | Molar Teeth | Maxillary | | | +30° |
| 4 | | Mandibular | | | -5° |
| 5 | Occlusal Plane | | | | +5°~+8° |

FIG. 5

<Lookup table: Radiographic mode 1 >

| Mode No. | Sensed angle value | Set value(X-ray emitting time) |
|---|---|---|
| 1 | +45 | t1 |
| 2 | -25 | t2 |
| 3 | +30 | t3 |
| 4 | -5 | t4 |
| 5 | +6.5 | t5 |

FIG. 6

X-RAY IRRADIATING DEVICE INCLUDING MOTION SENSOR AND X-RAY IMAGING METHOD USING SAME

CROSS REFERENCE TO RELATED APPLICATIONS

This application is a National Stage Patent Application of PCT International Patent Application No. PCT/KR2016/004101 (filed on Apr. 20, 2016) under 35 U.S.C. § 371, which claims priority to Korean Patent Application No. 10-2015-0055237 (filed on Apr. 20, 2015), the teachings of which are incorporated herein in their entireties by reference.

TECHNICAL FIELD

The present invention relates generally to an X-ray irradiating device and an X-ray imaging method using the same. More particularly, the present invention relates to an X-ray irradiating device of which a radiographer manually determines the position and orientation of the device to perform radiography, and to an X-ray imaging method using the same.

BACKGROUND ART

X-ray imaging is a radiography method using permeability of X-rays, and acquires an X-ray image of an internal structure of a subject to be imaged based on the attenuation that is accumulated in the process of the X-rays passing through the subject. To achieve this, an X-ray imaging apparatus includes: an X-ray irradiating device emitting X-rays; an X-ray sensor disposed to face the X-ray irradiating device with a subject therebetween, and configured to receive the X-rays having passed through the subject; and an image processor configured to produce an X-ray image by using a detection result of the X-ray sensor. The X-ray irradiating device has been continuously reduced in size and improved in convenience. Recently, compact X-ray irradiating devices, which can be easily used by radiographers, has been frequently used for diagnosis in a hospital or nondestructive examination in an industrial field.

As an example, this compact X-ray irradiating device is also used for intraoral radiography in the dental field. When it is required to perform quick radiography for an examinee having difficulty in moving during an implant procedure or the like, a hand-held type X-ray irradiating device or a compact X-ray irradiating device connected to an instrument called as a standard arm is used. During intraoral radiography, a compact X-ray sensor or a film is inserted into an examinee's mouth, and a radiographer performs radiography by irradiating X-rays toward the inserted X-ray sensor while holding the X-ray irradiating device by hand.

However, in performing intraoral radiography, it is necessary to adjust the dose of X-ray radiation according to the position and size of teeth, etc. of a subject, the size of an examinee's body, and the like. To achieve this, the radiographer performs a process of changing the setting of the X-ray irradiating device through an input means including a button or a touch interface before radiography. In this case, the radiographer sets the radiographic mode with one hand while holding the X-ray irradiating device with the other hand in the state where the intraoral X-ray sensor is inserted into the examinee's mouth. This process causes inconvenience in both the examinee with the X-ray sensor inserted into the mouth while waiting and the radiographer manipulating the input means while holding the heavy X-ray irradiating device with one hand.

DISCLOSURE

Technical Problem

Accordingly, the present invention has been made keeping in mind the above problems occurring in the related art, and an object of the present invention is to provide an X-ray irradiating device and an X-ray imaging method using the same, in which a radiographic mode suitable for a subject is automatically set in preparation for radiography while a radiographer holds the device without the need to operate a separate input means.

Technical Solution

In order to achieve the above object, according to some aspects of the present invention, there is provided an X-ray irradiating device includes: an X-ray source; a motion sensor configured to detect a X-ray source pointing direction; and a controller configured to select any one of a plurality of radiographic modes according to a pointing angle signal received from the motion sensor.

The controller may control a dose of X-ray radiation emitted from the X-ray source for radiographing to a different set value according to the selected radiographic mode.

Here, the X-ray irradiating device may further include a memory connected to the controller, and configured to store a lookup table including the set values for the dose of X-ray radiation which are corresponding to the radiographic modes determined by the pointing angle signal.

The controller may control the dose of X-ray radiation by controlling at least one of X-ray emitting time, tube voltage, and tube current of the X-ray source for radiographing.

Further, the X-ray irradiating device according to the present invention may further include: an auxiliary beam emitter configured to indicate the X-ray source pointing direction, by emitting a visible ray; and a reference plane set button configured to set the X-ray source pointing direction as a reference value for calculating the pointing angle signal with a radiographer's input.

Meanwhile, the controller may detect a pattern of motion by using the motion sensor, and select a radiographic mode according to the detected pattern of motion.

An X-ray imaging method according to the present invention, which uses the above described X-ray imaging device, includes: setting a reference plane as a reference value for a pointing angle in which an X-ray source is directed; detecting the pointing angle relative to the reference plane by using a gyro sensor, and selecting a radiographic mode corresponding to the detected pointing angle; and performing a radiography by controlling the X-ray source with a preset value corresponding to the selected radiographic mode.

The selecting the radiographic mode may include: selecting the radiographic mode corresponding to the detected pointing angle with reference to a lookup table input in advance in a memory of an X-ray irradiating device when the pointing angle relative to the reference plane is detected by the gyro sensor, and loading the set value according to the selected radiographic mode to a controller of the X-ray irradiating device.

Meanwhile, the X-ray imaging method according to the present invention may further include: detecting a pattern of motion of an X-ray irradiating device by using the motion sensor, and selecting a radiographic mode according to the detected pattern of motion.

Advantageous Effects

According to the present invention configured as describe above, it is advantageous in that a radiographic mode suitable for a subject is automatically set in preparation for radiography while a radiographer holds the device without the need to operate a separate input means, whereby it is possible to increase the convenience of a radiographer. It is further advantageous in that the time spent in selecting and inputting the radiographic mode is eliminated, thus it is possible to reduce waiting time of an examinee.

MODE FOR INVENTION

Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

Figure 1:
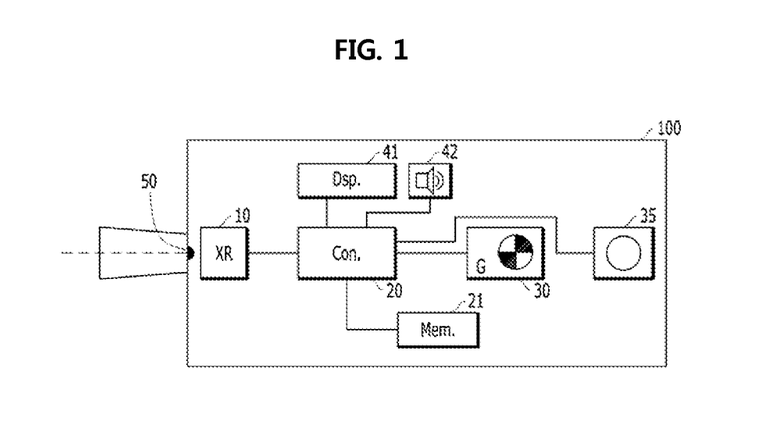
FIG. 1 schematically shows a configuration of an X-ray irradiating device according to an embodiment of the present invention.

FIG. 1 schematically shows a configuration of an X-ray irradiating device according to an embodiment of the present invention.

An X-ray irradiating device 100 according to the embodiment includes: an X-ray source 10 emitting an X-ray beam in a predetermined direction; a motion sensor 30 configured to detect a X-ray source pointing direction, that is, a pointing angle at which the X-ray beam is emitted, by detecting the position of the device body relative to a direction of gravity; and a controller 20 configured to select any one of a plurality of radiographic modes according to the pointing angle signal received from the motion sensor 30. Herein, it is preferred that the motion sensor 30 include at least one of a gyro sensor, an acceleration sensor, and a geomagnetic sensor.

In order to select the above described radiographic mode, the X-ray irradiating device 100 according to the embodiment may further include a memory 21 that is connected to the controller 20, and is configured to store a lookup table including the set values for the dose of X-ray radiation which are corresponding to the radiographic modes determined by the pointing angle signal. In other words, the controller 20 can look up a corresponding radiographic mode according to the reference value pre-input in the lookup table by using the data of the pointing angle received from the motion sensor 30, and can control the dose of X-ray radiation emitted from the X-ray source 10 for radiographing with each different set values according to the selected radiographic mode.

As an example of controlling the dose of X-ray emitted from the X-ray source 10 for radiographing, the controller 20 may control an X-ray emitting time to control the dose of X-ray radiation. As a method of controlling the dose of X-ray radiation, a method of controlling a tube voltage of the X-ray source 10, a method of controlling a tube current thereof, a method of controlling an emitting time based on the assumption that the tube voltage and the tube current are constant as in the embodiment, and the like may be used. These methods are more suitable for controlling an X-ray source of an electric field emission type having a nanostructure. The control of the emitting time may be performed in a pulse unit with a predetermined cycle.

Further, the X-ray irradiating device 100 according to the embodiment may further include an auxiliary beam emitter 50 configured to indicate the X-ray source pointing direction, by emitting a visible ray. The auxiliary beam emitter 50 may be, for example, in the form of a laser beam emitting device that emits a straight visible light laser beam in the form of a dot or a line, but is not limited thereto and may be implemented using a light source such as an LED having a narrow directivity angle.

Meanwhile, the X-ray irradiating device 100 according to the embodiment may further include a reference plane set button 35 configured to set the X-ray source pointing direction with a radiographer's input as a reference value for calculating the pointing angle signal with a radiographer's input. The reference plane set button is connected to the controller 20, and is provided outside the X-ray irradiating device 100 to allow the radiographer to easily operate the same. In addition, the X-ray irradiating device 100 according to the embodiment may further include: a display unit 41 configured to display the current status of the device, the selection result of the radiographic mode, or the like on a screen; and a speaker 42 configured to inform the radiographer of a situation such as selection of the radiographic mode.

The radiographer can position the X-ray irradiating device 100 while predicting an irradiating direction of the X-ray beam toward the examinee by using the visible light beam emitted from the auxiliary beam emitter 50. When the radiographer positions the X-ray irradiating device 100, the controller 20 identifies the pointing angle signal from the motion sensor 30 in real time or by the radiographer's input. When the radiographer presses the reference plane set button 35, the controller 20 identifies the plane including the X-ray irradiating direction of the X-ray irradiating device 100 as a reference plane, and after that, it identifies the value corresponding to the inclination angle with respect to the reference plane as the above-described pointing angle, thereby automatically selecting a radiographic mode.

Meanwhile, the controller 20 may detect a pattern of motion by using the motion sensor 30 and select a radiographic mode according to the detected pattern of motion, as well as select radiographic mode described above. This function can be implemented in such a manner that signal patterns of the motion sensor 30 corresponding to several characteristic motion patterns are stored in the memory 21 in advance, and the controller 20 identifies the pattern.

Figure 2:
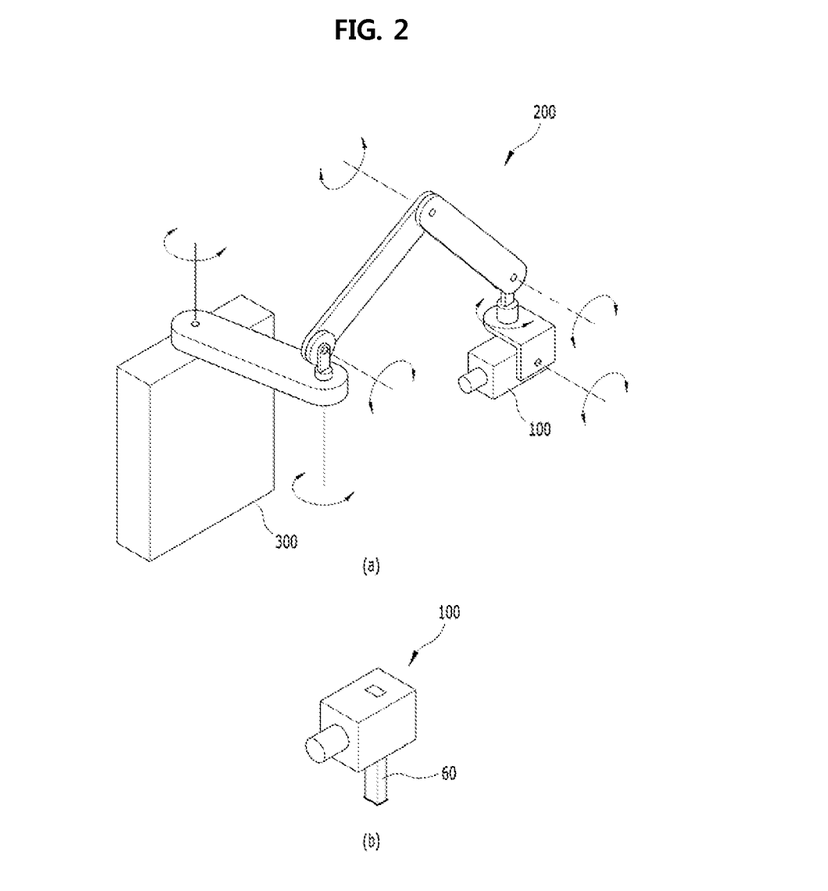
FIG. 2 shows an example of use of the X-ray irradiating device according to the present invention.

FIG. 2 shows an example of use of the X-ray irradiating device according to the present invention.

The X-ray irradiating device 100 according to the embodiment, as shown in FIG. 2A, may be utilized by being connected to a standard arm 200. The standard arm 200 connects the X-ray irradiating device 100 with a structure 300 fixed on a wall or the ground through multiple axis, and allows the radiographer to easily adjust the position of the X-ray irradiating device 100 while support the load thereof.

Meanwhile, the X-ray irradiating device 100 according to the embodiment, as shown in FIG. 2B, may be utilized in the movable form having a handle 60 to allow the radiographer to grip the handle by a hand. The shape of the handle 60 shown in the drawing is only one example, so various changes in the shape of the handle may be possible as long as it allows the radiographer to easily adjust the position of the X-ray irradiating device 100, that is, the irradiating direction of the X-ray beam. As another example, it may have a shape similar to a camera grip.

Hereinbelow, reference will be made to an X-ray imaging method using and X-ray irradiating device according to an embodiment of the present invention, with reference to FIGS. 3 to 6. The following description will not only help to understand the configuration of the X-ray imaging method according to one aspect of the present invention, but will also help to better understand the configuration of the X-ray imaging apparatus according to one aspect of the present invention.

Figure 3:
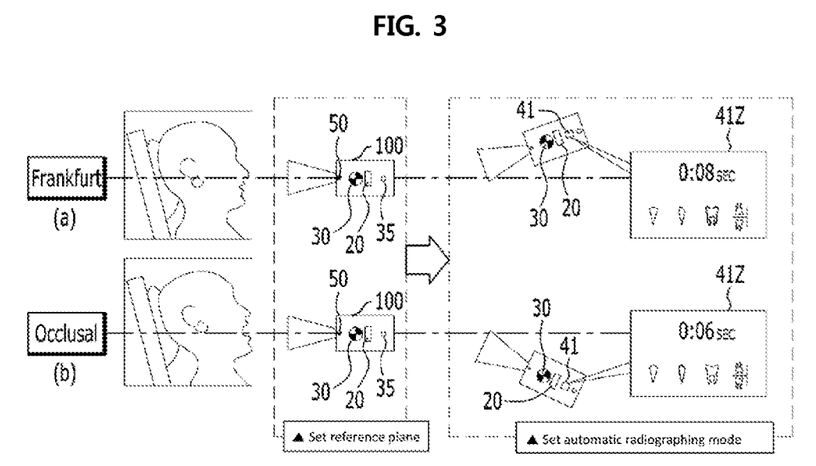
FIG. 3 shows an example of selecting an automatic radiographic mode using the X-ray irradiating device according to an embodiment of the present invention.

FIG. 3 shows an example of selecting an automatic radiographic mode using the X-ray irradiating device according to an embodiment of the present invention.

FIG. 3A schematically shows the process of radiographing maxillary molar teeth as an example. The radiographer aligns the irradiating direction of X-rays of the X-ray irradiating device 100 with the Frankfurt line by using the visible light beam of the auxiliary beam emitter 50, and sets the reference plane by pressing the reference plane set button 35. The controller 20 identifies the signal value of the motion sensor 30 in this position as the initial value representing the reference plane.

When the radiographer adjusts the position of the X-ray irradiating device 100 again such that a radiographing angle of the maxillary molar teeth, for example, an angle of about +30 degrees based on the Frankfurt line shown in the drawings is maintained for a predetermined time, the controller 20 identifies that the pointing angle is +30 degrees using the difference of the above described initial value of the signal value of the motion sensor 30. The controller 20 searches for the corresponding radiographic mode in the lookup table preset and stored in the memory by using the identified pointing angle, and automatically sets the radiographic mode. Here, the radiographic mode selection result and the corresponding set value may be displayed on the display unit 41 as shown in the enlarged view 41z. The controller 20 may load the set value for the dose of X-ray radiation or the X-ray emitting time corresponding to the selected radiographic mode from the memory, and may control the X-ray source accordingly. For example, for the radiographic mode of the maxillary molar teeth, it is possible to control the X-ray source to irradiate the X-ray beam for a preset time of 0.08 seconds. Meanwhile, the X-ray irradiating device 100 may inform the radiographer via sound through a speaker that the automatic radiographic mode has been selected.

FIG. 3B schematically shows the process of radiographing mandibular anterior teeth as another example. The radiographer aligns the position of the X-ray irradiating device 100 with the occlusal plane by using the auxiliary beam emitter 50, and sets the reference plane by pressing the reference plane set button 35. The controller 20 identifies the signal value of the motion sensor 30 in this position as the initial value representing the reference plane.

When the radiographer adjusts the position of the X-ray irradiating device 100 again such that a radiographing angle of the mandibular anterior teeth, for example, an angle of about −25 degrees based on the occlusal plane shown in the drawings is maintained for a predetermined time, the controller 20 automatically selects the mandibular anterior teeth radiographic mode through the procedures similar to those described above with reference to FIG. 3A, and controls the X-ray source using the corresponding set value. The set value of the X-ray beam emitting time corresponding to the radiographic mode shown in FIG. 3B may be different from that of FIG. 3A.

Figure 4:
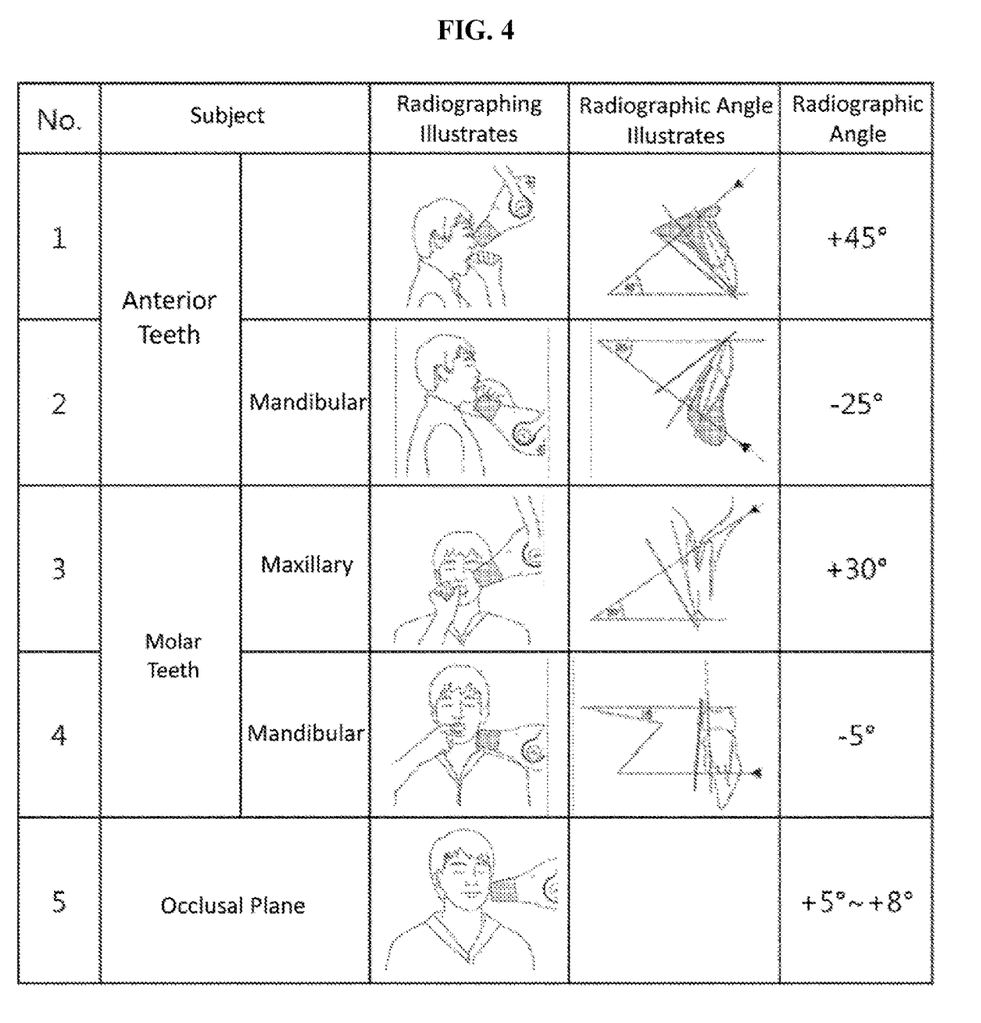
FIG. 4 shows an example of an appropriate radiographic angle according to a subject in intraoral radiography.

FIG. 4 shows an example of an appropriate radiographing angle according to a subject in intraoral radiography.

This drawing shows examples of various scenes of performing radiography of various subjects and the corresponding radiographing angles when performing radiography using the intraoral X-ray sensor and the X-ray irradiating device. The described radiographing angle is an example of a representative value or a range of angles recommended for radiographing for each subject, and the reference plane may be different from each other. It can be understood from this drawing that the appropriate radiographing angles are different for each tooth to be radiographed and it can be used as a reference value for selecting the radiographic mode.

Figure 5:
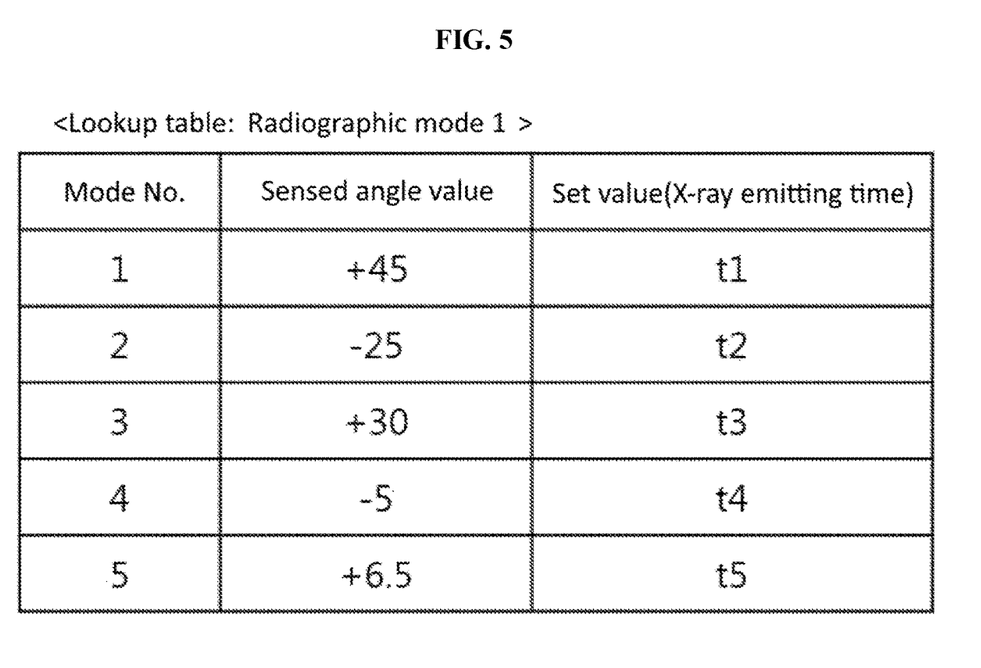
FIG. 5 shows an example of a lookup table for the automatic radiographic mode used for an X-ray imaging device and an X-ray imaging method using the same according to an embodiment of the present invention.

FIG. 5 shows an example of a lookup table for the automatic radiographic mode used for an X-ray imaging apparatus and an X-ray imaging method using the same according to an embodiment of the present invention.

The lookup table shown in the drawing may include a radiographic mode to be selected according to a sensed angle value representing a pointing angle with respect to a reference plane, and a set value corresponding to the radiographic mode, for example, an X-ray emitting time. The lookup table may be processed into a predetermined data format readable by the controller and stored in the memory. Meanwhile, the lookup table shown here is only one example and may be modified into various forms. As an example of modification, the sensed angle value may be given in a predetermined range rather than a specific value. Further, the sensed angle value may be given as a unit of the signal value provided by the motion sensor, not the value converted to the actual angle. Further, the lookup table may include tube current and tube voltage information according to each radiographic mode, as a set value corresponding to the radiographic mode, separately or in parallel with the X-ray emitting time. There are many other variations available.

Figure 6:
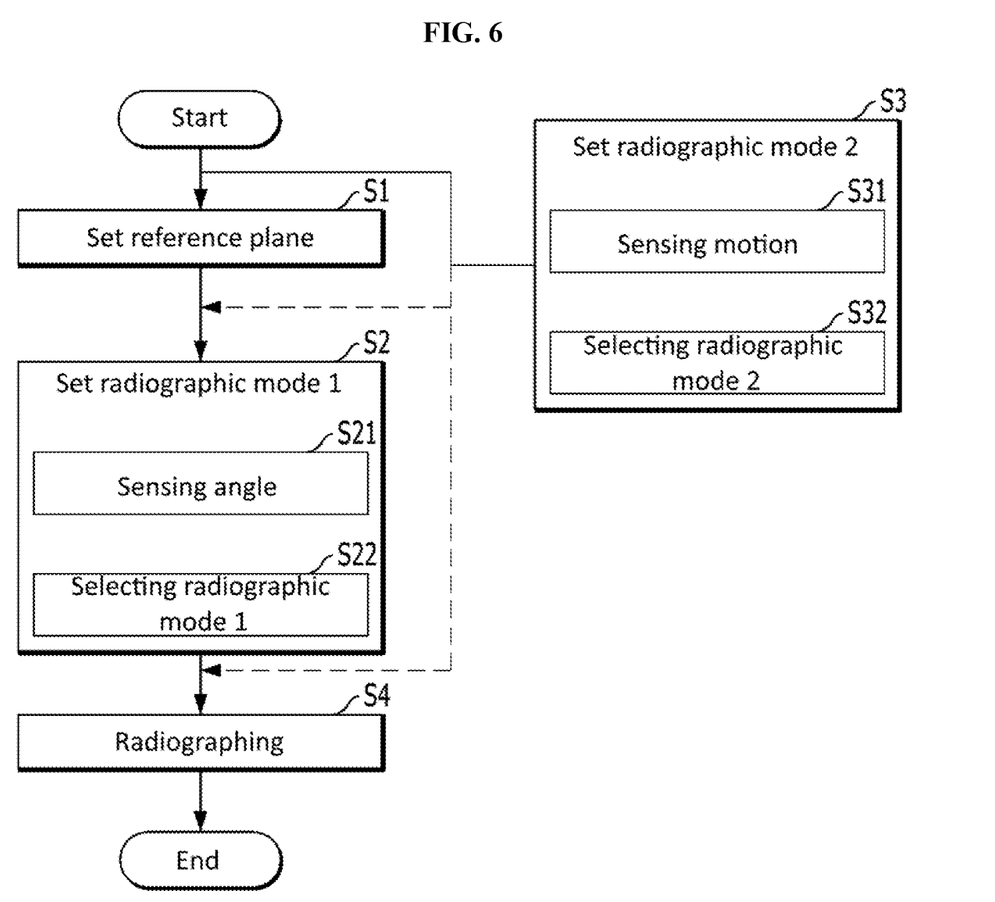
FIG. 6 shows an example of the X-ray imaging method according to an embodiment of the present invention.

FIG. 6 shows an example of the X-ray imaging method according to an embodiment of the present invention.

The X-ray imaging method according to the present invention uses the above described X-ray imaging apparatus, and includes: setting a reference plane as a reference value for a pointing angle in which an X-ray source is directed; detecting the pointing angle relative to the reference plane by using a motion sensor, and selecting a radiographic mode corresponding to the detected pointing angle; and performing radiography by controlling the X-ray source with a preset value corresponding to the selected radiographic mode. Meanwhile, the X-ray imaging method according to the present invention may further include a step of selecting another automatic radiographic mode, that is, detecting a pattern of motion such as shaking or tilting the X-ray irradiating device by using the motion sensor, and selecting a radiographic mode according to the detected pattern of motion.

The step of selecting the radiographic mode may include selecting the radiographic mode corresponding to the detected pointing angle with reference to a lookup table pre-input in a memory of an X-ray irradiating device when the pointing angle relative to the reference plane is detected by the motion sensor, and loading the set value according to the selected radiographic mode to a controller of the X-ray irradiating device.

Herein, a group of radiographic modes, which vary according to the size and position of the teeth to be radiographed, is defined as radiographic mode 1, and a group of radiographic modes, which vary according to the age and body size of the examinee, is defined as radiographic mode 2, which will be described in more detail as follows. The step of setting the reference plane (S1) has been described hereinbefore, with reference to FIG. 3. As the step of automatically setting the radiographic mode 1 (S2), the step of sensing an angle by using the motion sensor (S21), and the step of automatically selecting the radiographic mode 1 by identifying the tooth to be radiographed according to the sensed angle are also the same as described above.

Meanwhile, the step of automatically setting the radiographic mode 2 (S3) may be performed before or after the step of setting the reference plane (S1) or after the step of automatically setting the radiographic mode 1 (S2). The step of automatically setting the radiographic mode 2 (S3) may include the step of sensing a motion such as shaking or tilting the X-ray imaging apparatus by using a motion sensor (S31), and the step of automatically selecting the radiographic mode 2 according to the sensed pattern of motion (S32).

Even if the tooth at the same location is the subject, the dose of X-ray radiation may vary depending on whether the examinee is an adult or a child, and depending on the head size and weight of the examinee. The radiographic mode 2 may be classified into, for example, an adult radiographic mode, a child radiographic mode, and an obese radiographic mode in consideration of these characteristics. According to the classification of the radiographic mode 2, it is possible to collectively adjust the set value according to the radiographic mode 1 by a predetermined ratio or an offset value.

The various motion patterns may be quantified or functioned as characteristic patterns of the signal value of the motion sensor, and the quantified or functioned patterns of the signal value may be stored in the memory in the form of a lookup table for the radiographic mode 2 and utilized in the same manner as in the selection of the radiographic mode 1. In addition, algorithms for identifying motion patterns from patterns of the signal value of the motion sensor may be implemented in a variety of ways.

INDUSTRIAL APPLICABILITY

The present invention may be used directly in the field of dental radiography.

The invention claimed is:

1. An X-ray irradiating device comprising:
an X-ray source to emit X-rays;
an auxiliary beam emitter configured to indicate a pointing direction of the X-ray source by emitting a visible ray;
a motion sensor configured to detect the visible ray to determine the pointing direction of the X-ray source, and configured to set an angle of the pointing direction of the X-rays source as a reference value for calculating a pointing angle signal; and
a controller configured to select a radiographic mode based on the pointing angle signal received from the motion sensor, and configured to control a dose of X-ray radiation emitted from the X-ray source for radiographing with set values based on the selected radiographic mode.

2. The X-ray irradiating device of claim 1, further comprising:
a memory connected to the controller and configured to store a lookup table including the set values for the dose of X-ray radiation corresponding to the radiographic mode.

3. The X-ray irradiating device of claim 1, wherein the controller controls the dose of X-ray radiation by controlling at least one of an X-ray emitting time, a tube voltage, and a tube current of the X-ray source.

4. The X-ray irradiating device of claim 1, wherein the controller detects a motion pattern by using the motion sensor, and selects the radiographic mode based on the detected pattern of motion.

5. The X-ray irradiating device of claim 1, wherein the controller identifies a plane including the X-ray irradiating direction of the X-ray irradiating device as a reference plane.

6. The X-ray irradiating device of claim 5, wherein the controller identifies the pointing angle when the X-ray source pointing direction is maintained for a predetermined time.

7. The X-ray irradiating device of claim 5, wherein the reference plane is a Frankfrut line or an occlusal surface.

8. The X-ray irradiating device of claim 1, wherein the radiographic mode is defined into at least two groups.

9. The X-ray irradiating device of claim 1, further comprising:
a display unit configured to display the selected radiographic mode.

10. An X-ray imaging method by an X-ray irradiating device, comprising:
determining a pointing direction of an X-ray source of the X-ray irradiating device based on a detected emitted visible light;
setting a reference plane as a reference value for a pointing angle based on the pointing direction of the X-ray source;
detecting the pointing angle relative to the reference plane, and selecting a radiographic mode corresponding to the detected pointing angle; and
performing radiography by controlling the X-ray source with a preset value corresponding to the selected radiographic mode.

11. The X-ray imaging method of claim 10, wherein the selecting the radiographic mode includes:
selecting the radiographic mode corresponding to the detected pointing angle with reference to a lookup table, and loading the set value according to the selected radiographic mode.

12. The X-ray imaging method of claim 10, further comprising:
detecting a pattern of motion of the X-ray irradiating device, and selecting a radiographic mode according to the detected pattern of motion.

13. A device for irradiating an X-ray according to a plurality of radiographic modes, the device comprising:

an X-ray source configured to be controlled based on set values including an X-ray emitting time, a tube voltage, and a tube current;

a motion sensor configured to detect a pointing angle of the X-ray source relative to a predetermined reference plane; and a controller configured to select one radiographic mode of the plurality of radiographic modes, wherein:

the pointing angle varies depending on an object; and the controller selects the one radiographic mode based on the pointing angle and controls the X-ray source by adjusting the set values of the X-ray source for performing the selected radiographic mode.

14. The device of claim 13, further comprising:

a memory connected to the controller and configured to store a lookup table of the set values for performing the radiographic mode selected according to the pointing angle.

15. The device of claim 13, further comprising:

an auxiliary beam emitter configured to indicate the X-ray source pointing direction, by emitting a visible ray.

* * * * *